US011944797B2

(12) United States Patent
Cho et al.

(10) Patent No.: US 11,944,797 B2
(45) Date of Patent: Apr. 2, 2024

(54) DEVICE FOR ADJUSTING TIGHTENING ANGLE OF NEEDLE SAFETY PROTECTOR

(71) Applicant: PoongLim Pharmatech Inc., Gunsan (KR)

(72) Inventors: Hee Min Cho, Gunsan (KR); Mi Heui Cho, Gunsan (KR); Jong Deok Yun, Gunsan (KR); Jae Cheon Kim, Jeonju (KR)

(*) Notice: Subject to any disclaimer, the term of this patent is extended or adjusted under 35 U.S.C. 154(b) by 312 days.

(21) Appl. No.: 17/193,160

(22) Filed: Mar. 5, 2021

(65) Prior Publication Data

US 2022/0226584 A1 Jul. 21, 2022

(30) Foreign Application Priority Data

Jan. 18, 2021 (KR) .................. 10-2021-0006768

(51) Int. Cl.
*A61M 5/32* (2006.01)
*A61M 5/178* (2006.01)
*A61M 5/34* (2006.01)

(52) U.S. Cl.
CPC .......... *A61M 5/3202* (2013.01); *A61M 5/178* (2013.01); *A61M 5/3216* (2013.01); *A61M 5/34* (2013.01); *A61M 2205/273* (2013.01)

(58) Field of Classification Search
CPC ...... A61M 5/3202; A61M 5/34; A61M 5/178; A61M 5/3216; A61M 5/50; A61M 2205/273; A61M 2005/3217
See application file for complete search history.

(56) References Cited

U.S. PATENT DOCUMENTS 6,582,397 B2 6/2003 Alesi et al.
2003/0212369 A1* 11/2003 Kobayashi .......... A61M 5/3216
604/197

FOREIGN PATENT DOCUMENTS

KR 10-1076349 B1 10/2011
KR 10-1897956 B1 10/2018

* cited by examiner

*Primary Examiner* — Tasnim Mehjabin Ahmed
(74) *Attorney, Agent, or Firm* — KORUS Patent, LLC; Seong Il Jeong (57) ABSTRACT

A device for adjusting the tightening angle of a needle safety protector is proposed. The device is configured to provide an injection needle in an integrated state with a needle hub for preventing reuse of the injection needle and to fasten the needle hub to a needle safety protector that is disposed of in a folded state after use, a fastening structure is improved such that rotation is possible by a predetermined angle when the needle safety protector is rotated. Accordingly, an injection is safely performed by correcting the injection needle to the reference direction. In addition, even when a syringe is assembled by deviating from a reference angle during the mass production with the automatic line, the wrong angle is corrected in use.

1 Claim, 7 Drawing Sheets

Prior Art

FIG. 1

Prior Art

DEVICE FOR ADJUSTING TIGHTENING ANGLE OF NEEDLE SAFETY PROTECTOR

CROSS REFERENCE TO RELATED APPLICATION

The present application claims priority to Korean Patent Application No. 10-2021-0006768, filed Jan. 18, 2021, the entire contents of which is incorporated herein for all purposes by this reference.

BACKGROUND OF THE INVENTION

Field of the Invention

The present disclosure relates generally to a device for adjusting the tightening angle of a needle safety protector and, more particularly, to a device for adjusting the tightening angle of a needle safety protector, wherein the device may correct a direction of a cut portion of an injection needle to a predetermined direction when a needle hub holding the injection needle is fastened to the needle safety protector having a reuse prevention structure.

Description of the Related Art

In general, syringes are classified into a general type syringe and a Luer-lock type syringe. The general type syringe includes a barrel as a main body of a syringe, a push rod with a finger grip, a plunger fastened to a front end of the push rod and pushing injection liquid in a piston manner, and an injection needle fastened to a tapered tube at a front end of the barrel, and the Luer-lock type syringe has a structure in which a separate Luer-lock connector is provided to be screwed to the front end of the barrel and a hub to which the injection needle is mounted is screwed to the Luer-lock connector.

In the Luer-lock type syringe, a main body of the syringe and a needle hub to which an injection needle is mounted are separately manufactured. The needle hub to which the injection needle is mounted is sealed and sterilized in a separate needle storage casing, and the main body consisting of a barrel and a push rod is also sterilized and packaged in a kit configured as one set for storage and distribution. When the syringe is used, a sterile paper is removed from the needle storage casing, a screw portion famed on an inner surface of a Luer-lock connector famed on a front end of the syringe main body is aligned to fastening protrusions formed on both sides of a rear end of the needle hub and is turned, and then the syringe main body and the head portion are integrated to each other and the assembled syringe is separated from the needle storage casing to be used.

In the above method, syringes can be reused after use, and in some hospitals, transmission of injection by syringe reuse has become a social issue. In order to prevent this problem, a number of technique have been contrived to safely dispose of once used injection needles to prevent the used needles from being reused.

As an example, U.S. Pat. No. 6,582,397 B2 (Jun. 24, 2003) is proposed. In the related art, a groove receiving a flange is formed on a rear portion of a needle hub, a base has a hole, and a housing is connected to the base to be foldable. When the housing is folded while the needle hub is mounted to the base, an injection needle is inserted into the housing and arms formed on opposite sides of the base are aligned and fitted to locking grooves with tension formed at lower portions of opposite sides of the housing. When the housing is folded, the locking grooves with tension formed at the lower portions of the opposite sides of the housing are opened, and when the arms of the base is inserted into the locking grooves, the locking grooves are locked by tension recovery force not to be reopened, so that the used injection needle can be safely disposed of with a safety device. As another example, flaps protrude to be curved inward on opposite sides of the housing, so that the flaps are closed inward when the needle hub is inserted into the housing and the needle hub are prevented from being removed when the flaps are returned to the initial position by the recovery force. Therefore, the used injection needle can be safely disposed of with the safety device.

However, in the structure as described above, although the used injection needle may be disposed of with the hub and the safety device, the needle hub flange is simply fitted into the groove and hole of the base, so there is no clear countermeasure against the rotation in the hole. Furthermore, rotation can be prevented by a force-fitting method, but it is difficult to fit the needle hub tightly by the force fitting method because rotation adjusting is variable depending on the degree of force-fitting.

The fastening of the needle safety device and the needle hub is not performed manually, but is performed by an automatic device, so a tip of the injection needle is cut at an inclined angle to facilitate the injection into the human body and the cut surface is directed to the upper side when the injection needle is inserted into the human body.

Therefore, it is required to fasten the needle hub to the syringe main body in a predetermined direction.

However, when slight rotation occurs during insertion or attachment process so that the cut direction deviates from a predetermined direction during mounting of the injection needle to the needle hub, the fastening of the needle hub is performed in a wrong direction without a predetermined direction. Therefore, when the needle hub is fastened to the syringe main body for use, the cut surface of the injection needle is not directed in a different direction other than the upper side, which is a problem.

Figure 1:
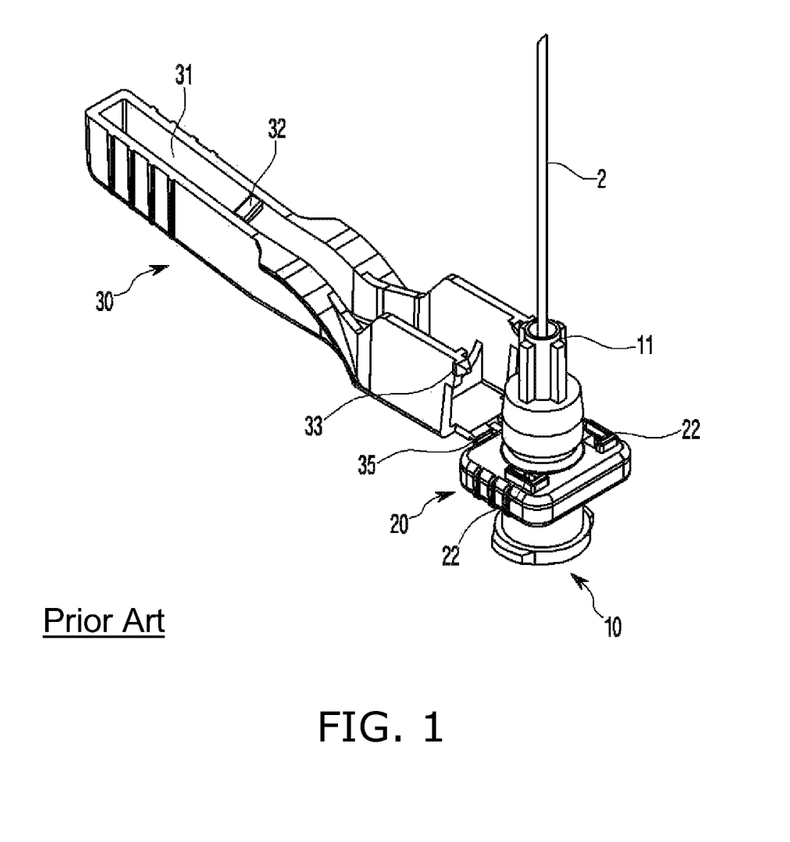
FIG. 1 is a perspective view showing a coupling state of a structure of the related art.
Figure 2:
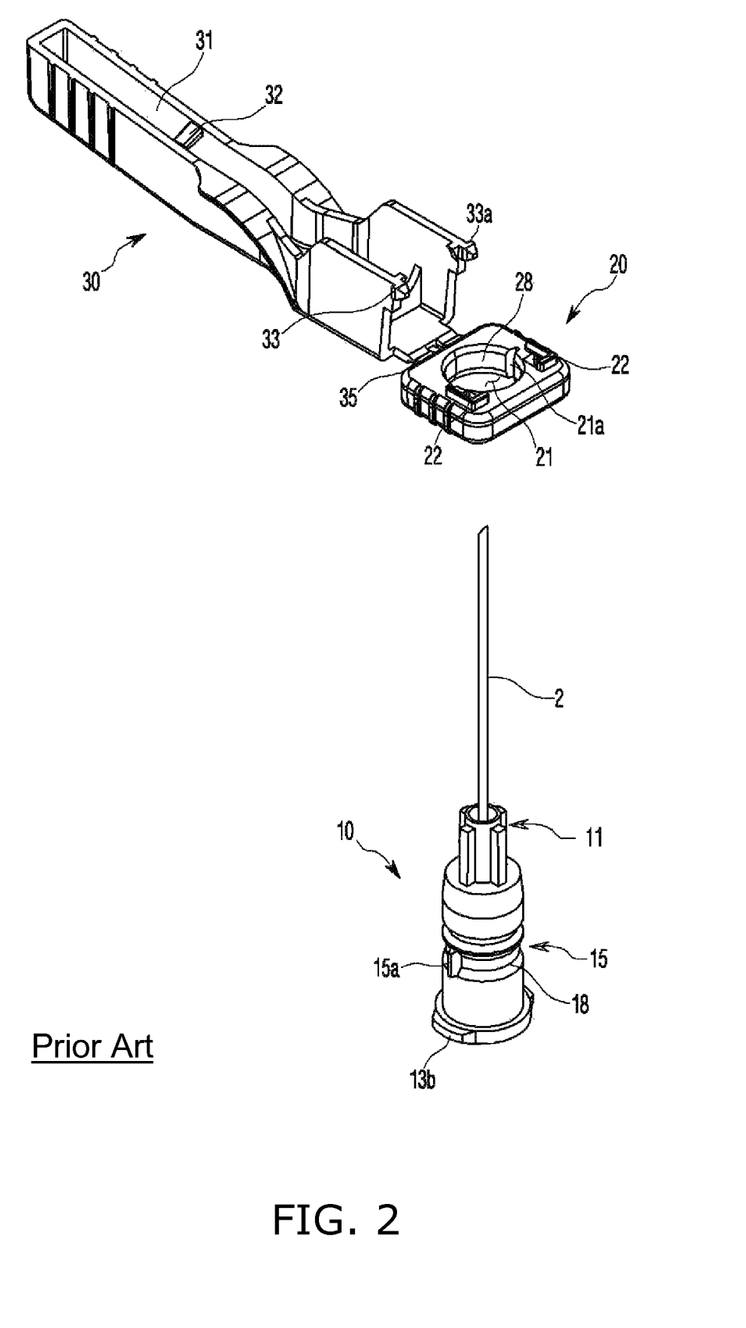
FIG. 2 is a perspective view showing a disassembled state of the structure of the related art.
Figure 3:
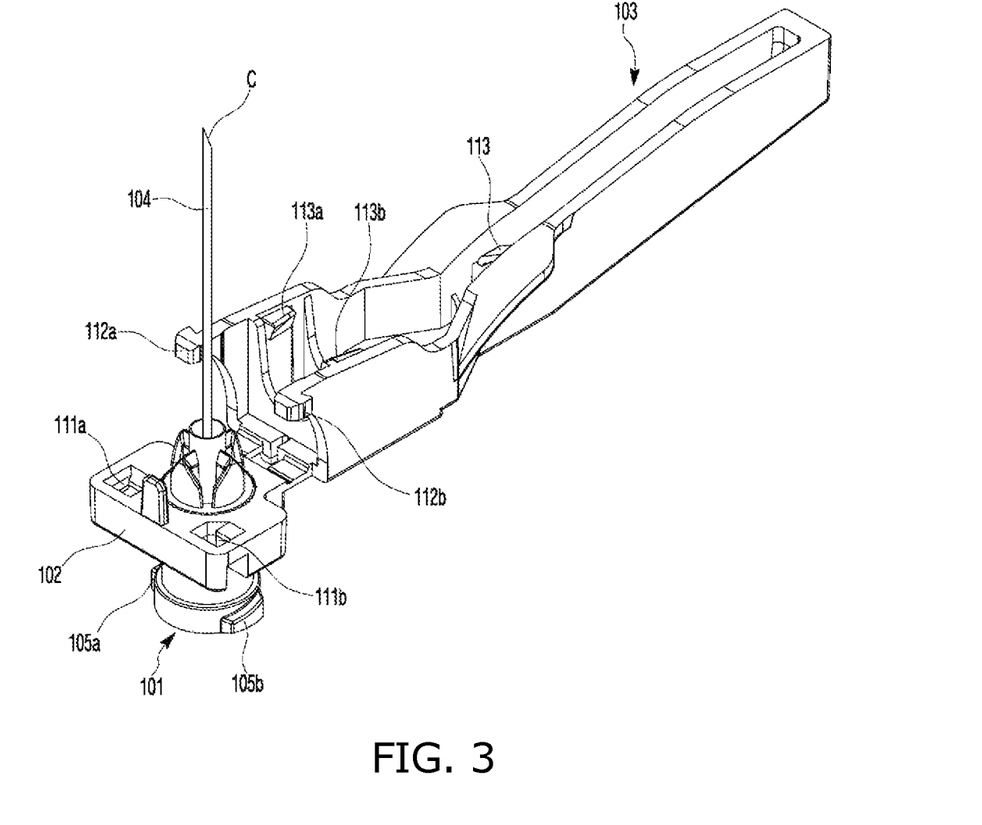
FIG. 3 is a side perspective view showing an assembled state of a device according to the present disclosure.
Figure 4:
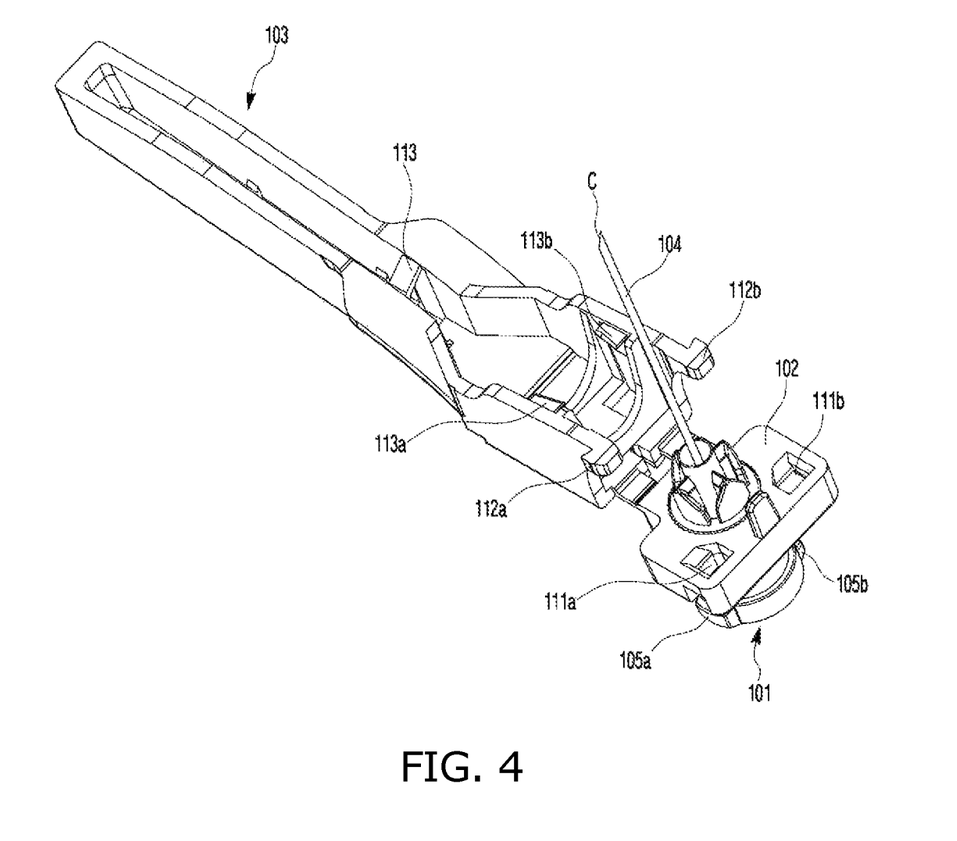
FIG. 4 is a plan perspective view showing the assembled state of the device according to the present disclosure.
Figure 5:
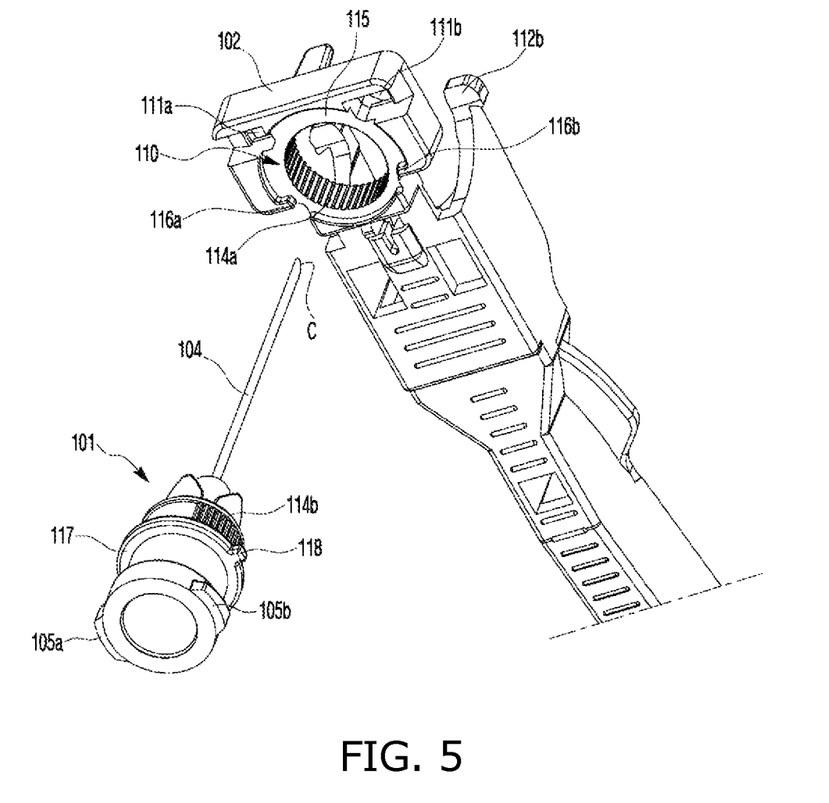
FIG. 5 is a lower perspective view showing a disassembled state of the device according to the present disclosure.
Figure 6:
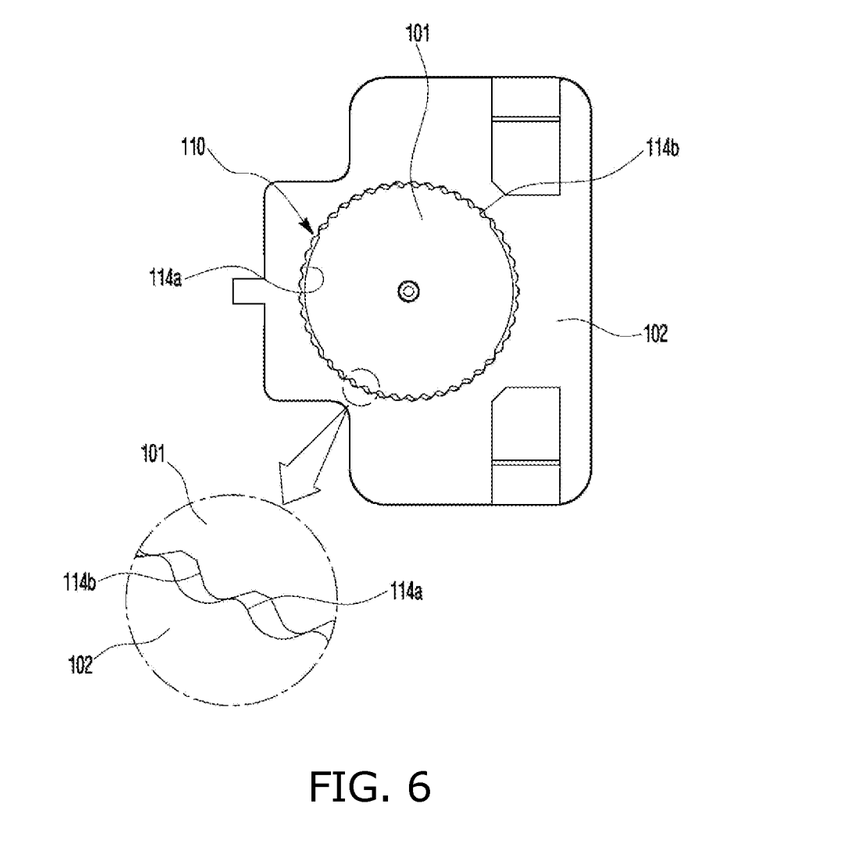
FIG. 6 is a sectional plan view showing an extracted main portion of an assembled state of the device according to the present disclosure.
Figure 7:
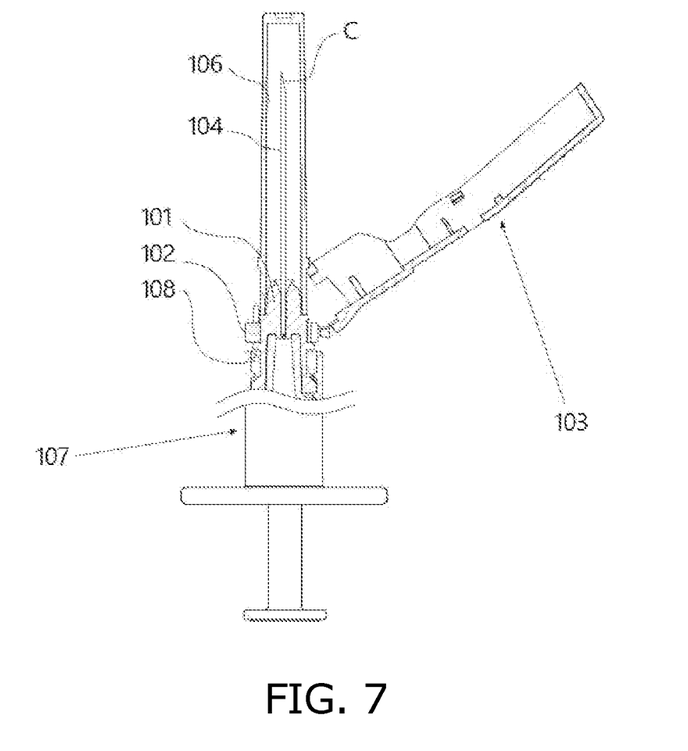
FIG. 7 is a side view with a partial sectional view showing an assembled state of a syringe barrel according to the present disclosure.

As another example, Korea Patent No. 10-1897956 "Needle assembly" is proposed as shown in FIG. 1. The needle assembly includes: a holder 10 holding an injection needle 2 and fastened to a needle protection cap 3 at a front side thereof and to a syringe 5 at a rear side thereof; a coupling device 20 having an insertion hole 21 provided coupling with a coupling portion 11 at the center of the holder 10, and having locking grooves 22 with locking steps 22a on opposite sides of an upper portion of the coupling device 20; and a cover 30 having an insertion space portion 31 integrally connected to one side of the coupling device 20 to be vertically rotated by a hinge 35, a supporting step 32 having an open side to allow the injection needle 2 to be inserted into the open side and to support the injection needle 2 inserted into the insertion space portion not to be separated therefrom, and locking protrusions 33 formed at opposite sides of a lower portion of the cover 30 and configured to be inserted into one of the locking grooves 22 of the coupling device 20, wherein when the injection needle is disposed of after use, a locking step 33a of one of the locking protrusions 33 is locked to the locking steps 22a to be prevented from separation, so that the injection needle may be disposed of safely and be prevented from being reused. A coupling portion 15 of the holder 10 consists of a ring-shaped concave portion 18, and a protrusion 28 is formed on an inner circumferential surface of the insertion hole 21 of the coupling device 20 to be inserted into the concave portion 18, so that the protrusion 28 is forcibly inserted into and fastened to the concave portion 18. A cut groove 21a is formed at one or more position of an inner surface of the insertion hole 21, and the coupling portion 15 has an insertion protrusion 15a at a position corresponding to the cut groove 21a so that the coupling device 20 and the holder 10 are fastened to each other to be prevented from rotation.

However, in the related art configured as described above, when the needle hub is fastened to the Luer-lock type syringe main body by screwing, the cut groove 21a is formed on the inner surface of the insertion hole 21 of the holder 10, and the holder 10 has the insertion protrusion 15a on the position corresponding to the cut groove 21a. When a locking protrusion 13b of the holder 10 is fastened to the Luer-lock screw portion of the syringe main body by screwing, the fastening is precisely performed without rotation at the fastening end point. However, as described above, when the injection needle 2 is mounted to the holder 10 in a wrong direction without the cut surface thereof facing the upper side, the mounted direction of the injection needle cannot be corrected with the above-described fastening structure, so the syringe is necessarily assembled and packaged while being mounted in a wrong direction. Accordingly, during use, the syringe is necessarily used with the cut portion not facing the upper side but being mounted in a wrong direction, and when the cut surface of the injection needle is directed to the lower side, the injection may occur by penetrating the skin of a patient in the wrong direction opposite the injecting direction, and this is a major problem that may cause a medical accident.

DOCUMENTS OF RELATED ART (Patent Document 1) U.S. Pat. No. 6,582,397 B2 (Jun. 24, 2003); and
(Patent Document 2) Korea Patent No. 10-1897956 (Sep. 6, 2018)

SUMMARY OF THE INVENTION

Accordingly, the present disclosure has been made keeping in mind the above problems occurring in the related art, and the present disclosure is intended to propose a device for adjusting the tightening angle of a needle safety protector. When a needle hub is fastened to a needle safety protector having a reuse prevention structure, even when an injection needle is mounted to the needle hub while a cut-off direction of an end of the injection needle is turned, the device is configured to have tooth protrusions that may be engaged and cross over each other so that the needle safety protector and the needle hub are fastened to each other in a coupling hole. Accordingly, even when a cut-off end portion of the injection needle is mounted with a wrong direction, an angle of the injection needle may be corrected.

In order to achieve the above objective, according to one aspect of the present disclosure, there is provided a device for adjusting the tightening angle of a needle safety protector. In the device, protrusions may be arranged at equal intervals on an inner surface of a hub coupling hole of a needle safety protector to which a needle hub is fastened, and protrusions may be formed in a circumference of a fastened body of the needle hub, wherein, when external force is applied to the protrusions of the needle safety protector and the protrusions of the needle hub coupled to each other to be rotated, the protrusions may be rotated to cross over each other, so that a cut surface of an end of an injection needle may be corrected to a predetermined direction.

According to the present disclosure, in providing the injection needle in an integrated state with the needle hub for preventing the reuse of the injection needle and in fastening the needle hub to the needle safety protector that is disposed of in a folded state after use, a fastening structure is improved such that rotation is possible by a predetermined angle when the needle safety protector is rotated. Therefore, even when the injection needle is fixed to the needle hub while a cut surface of a front end of the injection needle is rotated from the reference direction during a process of inserting and fastening the injection needle into the needle hub, the tightening angle can be adjusted while the Luer-lock connector at the front end of the syringe barrel is fastened to the needle hub, so that the injection can be safely performed by correcting the injection needle to the reference direction. In addition, even when the syringe is assembled by deviating from the reference angle during the mass production with the automatic line, the wrong angle can be corrected in use, so that usability and safety can be secured.

BRIEF DESCRIPTION OF THE DRAWINGS

The above and other objectives, features, and other advantages of the present disclosure will be more clearly understood from the following detailed description when taken in conjunction with the accompanying drawings, in which.

DETAILED DESCRIPTION OF THE INVENTION

The above and other objectives, features, and advantages of the present disclosure will be more clearly understood from the following detailed description taken in conjunction with the accompanying drawings.

In the flowing description, unless otherwise defined, all terms including technical and scientific terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Hereinbelow, a device for adjusting the tightening angle of a needle safety protector, the needle safety protector having a reuse prevention structure, according to an embodiment of the present disclosure will be described in detail with reference to accompanying drawings.

As shown in the drawings, according to the present disclosure, a device for adjusting the tightening angle of a needle safety protector having a reuse prevention structure is fundamentally configured like a conventional needle safety protector that is configured to safely dispose of a needle after use. The device for adjusting the tightening angle of a needle safety protector includes a needle hub 101, a needle safety protector main body 102, and a cover 103 connected integrally with the needle safety protector main body 102 to be foldable thereto.

An injection needle 104 is inserted into and fixed to a front portion of the needle hub 101, Luer-lock coupling protrusions 105a and 105b are formed by protruding on opposite sides of a rear portion of the needle hub 101, the injection needle 104 is protected by being covered with a needle cap 106, and the Luer-lock coupling protrusions 105a and 105b positioned at the rear portion of the needle hub 101 are fastened to a Luer-lock screw portion 108 formed at a front portion of a barrel 107 to constitute a syringe.

The cover 103 is connected to one side of the needle safety protector main body 102 while being foldable by a foldable connector 109 to be integrated with the needle safety protector main body 102. A hub coupling hole 110 is formed by vertically passing through the center of the needle safety protector main body 102. Cover coupling holes 111a and 111b are foiled on opposite sides of an upper portion of the needle safety protector main body 102, and locking steps 112a and 112b protrude outward on opposite sides of a lower portion of the cover 103 to be inserted and coupled to the cover coupling holes. On one side in the cover, a locking plate 113 horizontally protrudes to hold the needle cap 106 when the cover 103 is folded. Hub locking protrusions 113a and 113b protrude on the opposite sides of the lower portion of the cover 103 so that the needle cap 106 may be fitted therein, but is prevented from being separated from the cover 103. Therefore, the device for adjusting the tightening angle of a needle safety protector is configured to be safely disposed of together with the injection needle after use.

In the basic configuration as described above, on an inner circumferential surface of the hub coupling hole 110 vertically formed on the center portion of the needle safety protector main body 102, tooth protrusions 114a formed in semicircles on a plan sectional view are arranged at equal intervals in a circumference of the hub coupling hole 110. On a body surface of the needle hub 101 fitted into the hub coupling hole 110, tooth protrusions 114b formed in semi-circles on a plane sectional view are arranged at equal intervals in a circumference of the needle hub 101, so that the needle hub 101 is tightened to the needle safety protector main body 102 with the tooth protrusions 114a formed along the hub coupling hole 110 and the tooth protrusions 114b famed on the body surface of the needle hub 101 alternately engaged with each other.

The number of the tooth protrusions 114a, 114b is preferably formed at every 15° in the circumference, a total of 24. The height of each of the tooth protrusions 114a, 114b is preferably formed to the height in which the needle hub 101 and the barrel 107 in a fastened state cross over each other when external force is applied thereto by rotating the syringe with normal hand force.

Meanwhile, it is unnecessary to adjust the rotation angle to 360° in the circumference for the engagement between the tooth protrusions 114a and 114b. During use of the syringe assembly to inject medicine into the human body, injecting is performed while the needle hub 101 and the needle safety protector main body 102 are fastened to each other and the cover 103 is directed upward, so the cover 103 interferes with the injecting when being directed downward or to opposite sides thereof. Accordingly, it is necessary to control the rotation angle with respect to the engagement between the tooth protrusions 114a and 114b so that the tooth protrusions 114a and 114b are not rotated more than half the circumference to the left and right.

For achieving the above structure, a hub sliding flange inserting groove 115 is formed on the circumference of the hub coupling hole 110 at a lower surface of the needle safety protector main body 102, and a stopper 118 protrudes on a point of a sliding flange 117 formed at a rear circumference of the tooth protrusions 114b of the needle hub 101. An inner diameter of the hub sliding flange inserting groove 115 expands by a protruding length of the stopper 118 in order to insert the stopper 118 into the hub sliding flange inserting groove 115, and stopper locking steps 116a and 116b are formed on both left and right sides of the hub sliding flange inserting groove 115 to prevent the needle hub 101 from being rotated more than half the circumference to the left and right.

The present disclosure configured as described above is supplied while the needle safety protector main body 102 is fastened to the needle hub 101 as an all-in-one kit with the barrel 107. In use, the Luer-lock screw portion 108 formed at the front portion of the barrel 107 is aligned with the Luer-lock coupling protrusions 105a and 105b formed on the opposite sides of the rear portion of the needle hub 101 and then rotated. Whereby, the barrel 107 and the needle hub 101 are fastened to each other in a screwing manner so that the syringe is ready for use.

Before using the syringe by fastening the device and the barrel as described above, when the device is fastened in visually wrong direction other than a reference direction in which a direction of a cut-off surface C of the injection needle 104 is directed to the upper side, a user holds the needle safety protector main body 102 with one hand and rotates the barrel 107 with the other hand holding the barrel 107. Then, the tooth protrusions 114b protruding on an outer circumferential surface of a body of the needle hub 101 are rotated while crossing over the tooth protrusions 114a formed on the hub coupling hole 110 of the needle safety protector main body 102, so that the user can safely inject by aligning the direction of the cut-off surface C of the injection needle 104.

As described above, in addition that the user can directly adjust and use the syringe before injection, in the automatic packaging process line, it is possible to mechanically adjust the injection needle 104 that is fixed to the needle hub 101 while the direction of the cut-off surface C of the injection needle 104 is deviated from the reference direction. For example, when an optical sensor is applied to the cut-off surface C of the injection needle and light is prevented from passing through the injection needle, a rotation correction device may be operated to perform the rotation correction and therefore the packaging process may be carried out by aligning a direction uniformly.

When the syringe assembly is used for injecting into the human body, the needle hub 101 and the needle safety protector main body 102 should be controlled such that the needle hub 101 and the needle safety protector main body 102 coupled to each other with the cover 103 facing the upper side are not rotated more than half the circumference to the left and right. Therefore, as the hub sliding flange inserting groove 115 formed on the circumference of the hub coupling hole 110 at the lower surface of the needle safety protector main body 102 and the stopper 118 formed on one point of the sliding flange 117 formed on the rear circumference of the tooth protrusions 114b of the needle hub 101 are coupled to each other, the needle hub 101 may not be rotated more than half the circumference to the left and right.

As the optimal preferably embodiment of the present disclosure, the number of the tooth protrusions 114a and 114b in the present disclosure is suggested as 24 protrusions for each 15° of the circumference. However, the number of the tooth protrusions 114a and 114b may be provided to be more or less than 24 protrusions in response to the size and capacity of the syringe, and the protruding height of each of the tooth protrusions 114a and 114b may also be applied by designing various modifications in response to the situation within a range of heights in which the tooth protrusions 114a and 114b may cross over each other.

Although the invention is described with reference to specific items such as specific structural elements, to merely some embodiments, and to drawings, such specific details disclosed herein are merely representative for purposes of helping more comprehensive understanding of the present disclosure. The present disclosure, however, is not limited to only the example embodiments set forth herein, and those skilled in the art will appreciate that the present disclosure can be embodied in many alternate forms.

Accordingly, the present disclosure is intended to cover not only the exemplary embodiments, but also various alternatives, modifications, equivalents and other embodiments that may be included within the spirit and scope of the present disclosure as defined by the appended claims.

What is claimed is:

1. A device for adjusting the tightening angle of a needle safety protector, the needle safety protector having a reuse prevention structure, the device comprising:
   a needle hub (101); and
   a needle safety protector main body (102) and a cover (103) connected integrally with the needle safety protector main body (102) to be foldable thereto,
   wherein the device is configured such that, with the needle hub (101) tightened to the needle safety protector main body (102), a Luer-lock coupling protrusion (105a, 105b) of the needle hub (101) and a Luer-lock screw portion (108) formed at a front portion of a barrel (107) are tightened to each other so that injecting is performed while the barrel (107) and the needle safety protector main body (102) are coupled integrally to each other, and an injection needle (104) is covered with a needle cap (106), and the cover (103) is folded to the needle safety protector main body (102), and
   on an inner circumferential surface of a hub coupling hole (110) vertically formed at a center portion of the needle safety protector main body (102), tooth protrusions (114a) formed in semicircles on a plan section are arranged at equal intervals in a circumference of the hub coupling hole (110), and on a body surface of the needle hub (101) fitted in the hub coupling hole (110), tooth protrusions (114b) formed in semicircles on a plan section are arranged at equal intervals in a circumference of the needle hub (101), so that the needle hub (101) is tightened to the needle safety protector main body (102) with the tooth protrusions (114a) formed along the hub coupling hole (110) and the tooth protrusions (114b) formed on the body surface of the needle hub (101) alternately engaged with each other, wherein a hub sliding flange inserting groove (115) is formed on a circumference of the hub coupling hole (110) at a lower surface of the needle safety protector main body (102), and a stopper (118) is formed by protruding on a point of a sliding flange (117) formed at a rear circumference of the tooth protrusions (114b) of the needle hub (101), wherein an inner diameter of the hub sliding flange inserting groove (115) expands by a protruding length of the stopper (118) in order to insert the stopper (118) into the hub sliding flange inserting groove (115), and stopper locking steps (116a and 116b) are formed on both left and right sides of the hub sliding flange inserting groove (115) to prevent the needle hub (101) from being rotated more than half of the circumference to the left and right.

\* \* \* \* \*